(12) United States Patent
Lo et al.

(10) Patent No.: US 11,857,783 B2
(45) Date of Patent: Jan. 2, 2024

(54) IMPLANTABLE AND NON-INVASIVE STIMULATORS FOR GASTROINTESTINAL THERAPEUTICS

(71) Applicant: THE REGENTS OF THE UNIVERSITY OF CALIFORNIA, Oakland, CA (US)

(72) Inventors: Yi-Kai Lo, Los Angeles, CA (US); Wentai Liu, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 17/525,827

(22) Filed: Nov. 12, 2021

(65) Prior Publication Data
US 2022/0134100 A1    May 5, 2022

Related U.S. Application Data

(60) Division of application No. 16/437,359, filed on Jun. 11, 2019, now Pat. No. 11,202,907, which is a
(Continued)

(51) Int. Cl.
*A61N 1/36* (2006.01)
*A61N 1/05* (2006.01)
(Continued)

(52) U.S. Cl.
CPC ....... *A61N 1/36007* (2013.01); *A61N 1/0509* (2013.01); *A61N 1/36139* (2013.01);
(Continued)

(58) Field of Classification Search
CPC .............. A61N 1/36007; A61N 1/0509; A61N 1/36139; A61N 1/36167; A61N 1/37229;
(Continued)

(56) References Cited

U.S. PATENT DOCUMENTS 4,582,063 A * 4/1986 Mickiewicz ......... A61N 1/3603
607/66
4,785,812 A * 11/1988 Pihl ...................... A61N 1/3931
600/509
(Continued)

FOREIGN PATENT DOCUMENTS

CN    102500057 B    2/2014
WO    2004012812 A1   2/2004
(Continued)

OTHER PUBLICATIONS

European Patent Office (EPO), Communication (extended European search report), dated Aug. 19, 2020, related European patent application No. EP 17881353.1, pp. 1-9, claims searched, pp. 10-13.
(Continued)

*Primary Examiner* — Catherine M Voorhees
(74) *Attorney, Agent, or Firm* — O'BANION & RITCHEY LLP; John P. O'Banion

(57) ABSTRACT

Systems and methods for implementation of a disposable miniaturized implant for treatment of Post-Operative Ileums (POI), a miniaturized implant for treating chronic GI dysmotility (e.g., dysphagia, gastroesophageal reflux disease (GERD), nausea, functional dyspepsia, blockage of transit, and gastroparesis, inflammatory bowel disease) and obesity, by providing electrical stimulation to the part of bowel going through surgery to expedite the healing process while recording the smooth muscle activities simultaneously, or providing stimulation on a treatment location of the GI tract or the branch of the vagus nerve. Systems and methods are also provided for non-invasive, transcutaneous stimulation of anatomy within the abdomen of the patient.

20 Claims, 10 Drawing Sheets

Related U.S. Application Data continuation of application No. PCT/US2017/065917, filed on Dec. 12, 2017.

(60) Provisional application No. 62/433,122, filed on Dec. 12, 2016.

(51) Int. Cl.
  *A61N 1/375* (2006.01)
  *A61N 1/372* (2006.01)

(52) U.S. Cl.
  CPC ...... *A61N 1/36167* (2013.01); *A61N 1/37229* (2013.01); *A61N 1/37235* (2013.01); *A61N 1/37518* (2017.08)

(58) Field of Classification Search
  CPC .. A61N 1/37235; A61N 1/37518; A61N 1/36; A61N 1/36053; A61N 1/36057; A61N 1/36146; A61N 1/3756
  See application file for complete search history.

(56) References Cited

U.S. PATENT DOCUMENTS

| | | | |
|---|---|---|---|
| 5,154,183 A * | 10/1992 | Kreyenhagen | A61N 1/0587 600/375 |
| 6,191,156 B1 | 2/2001 | Kifor | |
| 6,567,695 B1 * | 5/2003 | Gruzdowich | A61N 1/0408 607/2 |
| 6,631,296 B1 | 10/2003 | Parramon | |
| 8,364,269 B2 | 1/2013 | Imran | |
| 11,202,907 B2 | 12/2021 | Lo | |
| 2001/0031999 A1 * | 10/2001 | Carter | A61N 1/36021 607/69 |
| 2002/0123771 A1 * | 9/2002 | Ideker | A61N 1/3622 607/14 |
| 2005/0131486 A1 | 6/2005 | Boveja | |
| 2005/0131487 A1 | 6/2005 | Boveja | |
| 2005/0137644 A1 | 6/2005 | Boveja | |
| 2005/0209653 A1 | 9/2005 | Herbert | |
| 2006/0178703 A1 | 8/2006 | Huston | |
| 2006/0199560 A1 | 9/2006 | Crivelli | |
| 2007/0103314 A1 | 5/2007 | Geissler | |
| 2008/0234599 A1 | 9/2008 | Chiao | |
| 2008/0300654 A1 | 12/2008 | Lambert | |
| 2008/0306359 A1 | 12/2008 | Zdeblick | |
| 2008/0312712 A1 | 12/2008 | Penner | |
| 2009/0004525 A1 * | 1/2009 | Fukushima | C07C 311/48 562/42 |
| 2009/0105784 A1 | 4/2009 | Massoud-Ansari | |
| 2009/0143831 A1 | 6/2009 | Huston | |
| 2009/0182318 A1 * | 7/2009 | Abboud | A61B 18/00 606/21 |
| 2010/0090338 A1 | 4/2010 | Lee | |
| 2010/0152817 A1 | 6/2010 | Gillbe | |
| 2010/0191311 A1 | 7/2010 | Scheiner | |
| 2010/0280573 A1 | 11/2010 | Schouenborg | |
| 2011/0034376 A1 | 2/2011 | Lubbers | |
| 2011/0077698 A1 | 3/2011 | Tsampazis | |
| 2011/0125203 A1 | 5/2011 | Simon | |
| 2012/0095531 A1 | 4/2012 | Derbas | |
| 2013/0090712 A1 * | 4/2013 | Popovic | A61N 1/0476 607/148 |
| 2013/0096651 A1 | 4/2013 | Ozawa | |
| 2014/0039579 A1 | 2/2014 | Adi | |
| 2014/0107726 A1 | 4/2014 | Voznesensky | |
| 2014/0180351 A1 * | 6/2014 | Gilman | A61N 1/39622 607/4 |
| 2014/0214124 A1 | 7/2014 | Greiner | |
| 2014/0220422 A1 | 8/2014 | Rogers | |
| 2014/0257438 A1 | 9/2014 | Simon | |
| 2014/0316484 A1 * | 10/2014 | Edgerton | A61N 1/0456 607/46 |
| 2015/0045810 A1 | 2/2015 | Hoffer | |
| 2015/0057718 A1 | 2/2015 | Sharma | |
| 2015/0066098 A1 | 3/2015 | Peterson | |
| 2015/0094788 A1 | 4/2015 | Pierenkemper | |
| 2015/0127068 A1 | 5/2015 | Simon | |
| 2015/0231396 A1 | 8/2015 | Burdick | |
| 2015/0241447 A1 | 8/2015 | Zitnik | |
| 2015/0343211 A1 | 12/2015 | Tal | |
| 2016/0045162 A1 | 2/2016 | De Graff | |
| 2016/0121108 A1 | 5/2016 | Kondo | |
| 2016/0158542 A1 | 6/2016 | Ahmed | |
| 2016/0243358 A1 * | 8/2016 | Creasey | A61N 1/0476 |
| 2018/0345011 A1 * | 12/2018 | Lo | A61N 1/3727 |

FOREIGN PATENT DOCUMENTS

| | | | | |
|---|---|---|---|---|
| WO | WO-2009111142 A3 * | 10/2009 | | A61N 1/05 |
| WO | 2010005482 A1 | 1/2010 | | |
| WO | 2015139053 A1 | 9/2015 | | |
| WO | 2015168162 | 11/2015 | | |
| WO | 2015168162 A1 | 11/2015 | | |
| WO | 2016065342 A1 | 4/2016 | | |
| WO | 2016073728 A1 | 5/2016 | | |
| WO | 2017091828 | 6/2017 | | |
| WO | 2017132566 A1 | 8/2017 | | |
| WO | 2018111943 | 6/2018 | | |

OTHER PUBLICATIONS

European Patent Office (EPO), Communication pursuant to Rules 70(2) and 70a(2) EPC (supplementary European search report) dated Oct. 11, 2019, related European patent application No. 16869351.3, pp. 1-6, claims searched, pp. 7-10.

ISA/US, United States Patent and Trademark Office (USPTO), International Search Report and Written Opinion dated Apr. 19, 2018, related PCT international application No. PCT/US2017/065917, pp. 1-10, claims searched, pp. 11-19.

Korean Intellectual Property Office (KIPO), International Search Report and Written Opinion dated Mar. 13, 2016, related PCT international application No. PCT/US2016/063886, pp. 1-15, claims searched, pp. 16-21.

Lo, Yi-Kai et al., "A 176-Channel 0.5cm3 0.7g Wireless Implant for Motor Function Recovery after Spinal Cord Injury", ISSCC 2016 / Session 22 / System and Instruments for Human-Machine Interfaces / 22.2, 2016 IEEE International Solid-State Circuits Conference, Feb. 3, 2016, pp. 382-384.

European Patent Office (EPO), Communication (extended European search report), dated Oct. 24, 2023, related European patent application No. EP 23183442.5, pp. 1-8, claims searched, pp. 9-11.

* cited by examiner

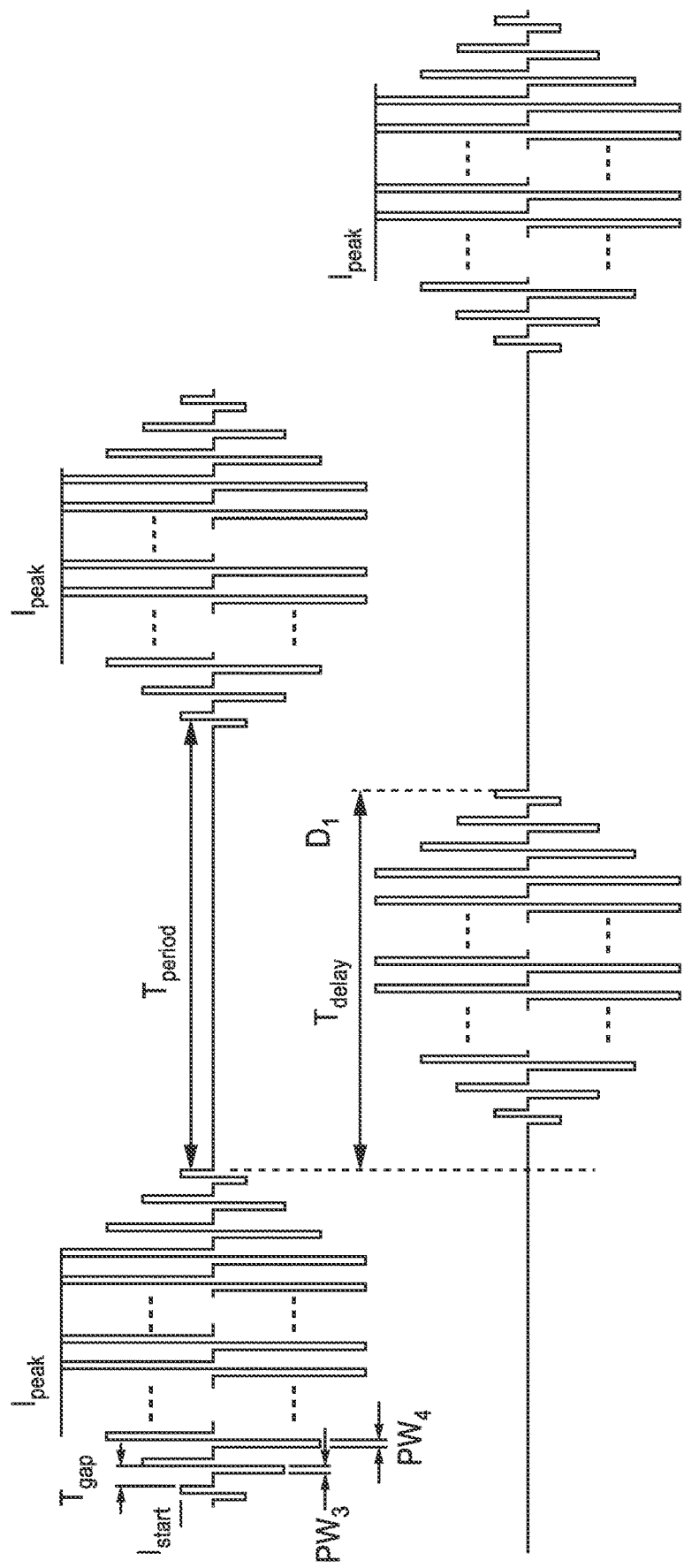

IMPLANTABLE AND NON-INVASIVE STIMULATORS FOR GASTROINTESTINAL THERAPEUTICS

CROSS-REFERENCE TO RELATED APPLICATIONS

This application is a division of U.S. patent application Ser. No. 16/437,359 filed on Jun. 11, 2019, which claims priority to, and is a 35 U.S.C. § 111(a) continuation of, PCT international application number PCT/US2017/065917 filed on Dec. 12, 2017, incorporated herein by reference in its entirety, which claims priority to, and the benefit of, U.S. provisional patent application Ser. No. 62/433,122 filed on Dec. 12, 2016, incorporated herein by reference in its entirety. Priority is claimed to each of the foregoing applications.

The above-referenced PCT international application was published as PCT International Publication No. WO 2018/111943 on Jun. 21, 2018, which publication is incorporated herein by reference in its entirety.

This application is related to PCT International Application No. PCT/US2016/063886 filed on Nov. 28, 2016 and published as WO 2017/091828 on Jun. 1, 2017, incorporated herein by reference in its entirety, which claims priority to, and the benefit of, U.S. provisional patent application Ser. No. 62/260,624 filed on Nov. 29, 2015, incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to therapeutic stimulation systems and methods, and more particularly to systems and methods for therapeutic stimulation in treatment of gastrointestinal disorders.

2. Background Discussion

Gastrointestinal neuromuscular disorder (GND) is a set of disorders characterized by the absence or poor function of the intestinal muscularis (IM), involving any segment of the gastrointestinal (GI) tract. GND may affect the enteric nervous system, smooth muscle cells, and/or the interstitial cells of Cajal (ICC), which are the pacemaker cells in the GI tract, thus resulting in functional GI diseases and dysmotility. Patients with GND may present with dysphagia, gastroesophageal reflux disease (GERD), nausea, functional dyspepsia, blockage of transit, and obstruction of the GI tract (e.g., gastroparesis), which accounts for 40% of GI tract illness that patients seek health care for in gastroenterology clinics. The current limitation in the treatment of GND associated GI dysmotility is the lack of understanding of the pathophysiology involving the neurons, ICC, and smooth muscle cells combined with the paucity of effective medications that can improve GI motility. The clinical alternative for pharmaceutically intractable GI dysmotility is usually the total or subtotal resection of the affected GI segments.

On the other hand, GI dysmotility can also be transiently induced through surgical operation (e.g., bowel resection surgery), leading to post-operative ileus (POI). POI leads to the inflammation of the bowel wall that occurs following abdominal surgery and its economic impact is estimated to be between $3/4 billion and $1 billion per year in the United States. Patients with POI manifest abdominal pain, nausea, vomiting, as well as the inability of coordinated propulsive mobility while the current treatment is restricted to the spontaneous recovery of the patient.

POI is not only limited to patients receiving abdominal surgery. There are patients receiving open-heart surgery also reporting symptoms similar to POI, possibly because the sympathetic and parasympathetic nerves governing the GI tack are affected by the surgery.

BRIEF SUMMARY

A primary premise of the system and methods disclosed herein is that electrical stimulation in the vagus nerve reduces the level of tumor necrosis factor (TNF), indicating the decrease of inflammation or the direct stimulation on the enteric nervous system and smooth muscles to adapting GI motility. Thus, an aspect of the present technology is a system and method configured to treat GI dysmotility through electrophysiological intervention by stimulating the bowel wall where the nerve ending of VN is located or the vagus nerve at the cervical or celiac branch. For the therapeutic treatment of POI that presents a transient GI dysmotility, the device performing stimulation is small and easily/conveniently removable after a course of POI treatment; for the diseases associated with chronic GI dysmotility, the miniaturized device can be implanted permanently.

In one embodiment, an SoC implant of the present description targets motor function of GI tract smooth muscles, with versatile functionalities and highly compact form factor (<0.5 cm$^3$ and <0.7 g) for various medical applications.

In another embodiment, anon-invasive, transcutaneous stimulation system is provided for stimulation of anatomy within the abdomen of the patient Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 9B is an image of a stepwise stimulus to mitigate stimulation edge effect according to the GI stimulation system and methods of the present description.

Figure 10A:
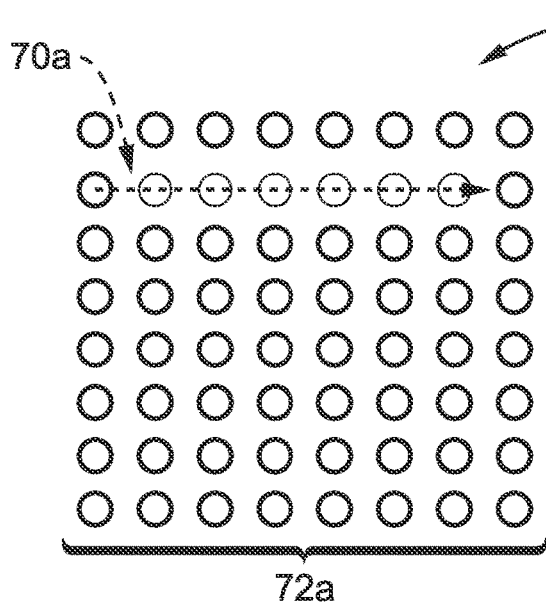
Figure 10B:
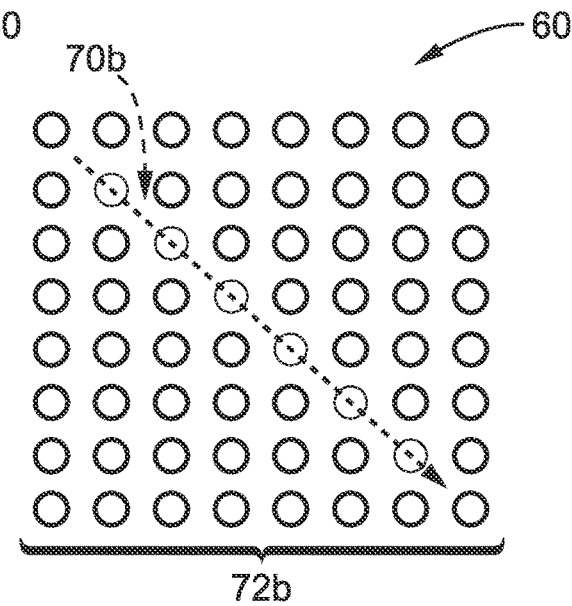
Figure 10C:
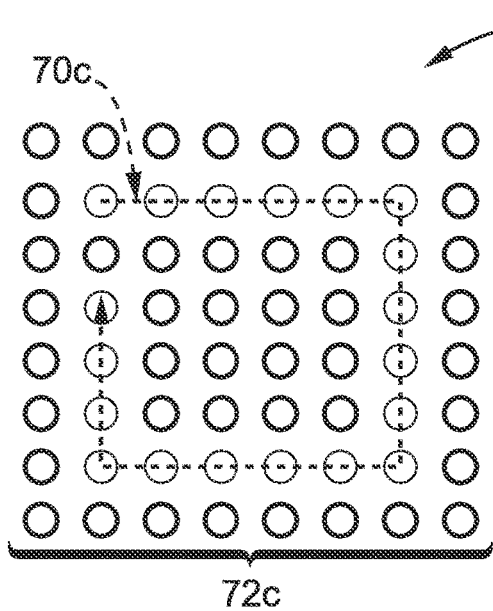
Figure 10D:
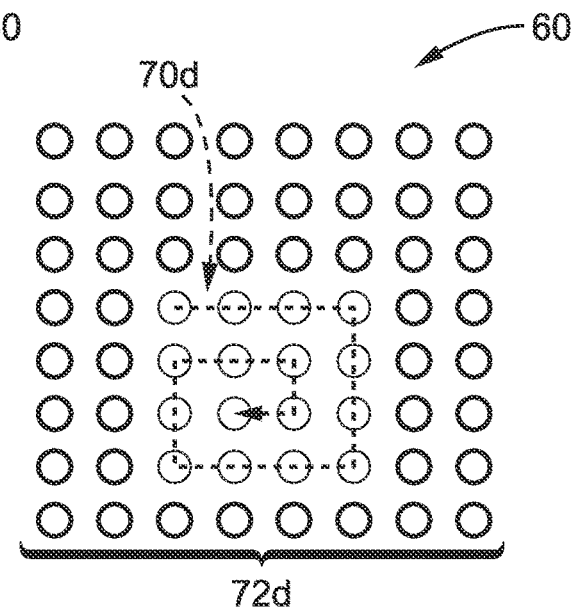

FIG. 10A through FIG. 10D show various stimulation current injection schemes in accordance with the present description (the arrow sign indicates the direction of onset sequence of the stimulation). An 8×8 electrode array is used as an example for illustration. FIG. 10A shows stimulated electrodes in an onset sequence of stimulation horizontally from left to the right. FIG. 10B shows stimulated electrodes in a diagonal onset sequence of stimulation. FIG. 10C shows stimulated electrodes in a clockwise rectangular onset sequence of stimulation. FIG. 10D shows stimulated electrodes in a clockwise spiral onset sequence of stimulation.

Figure 11:
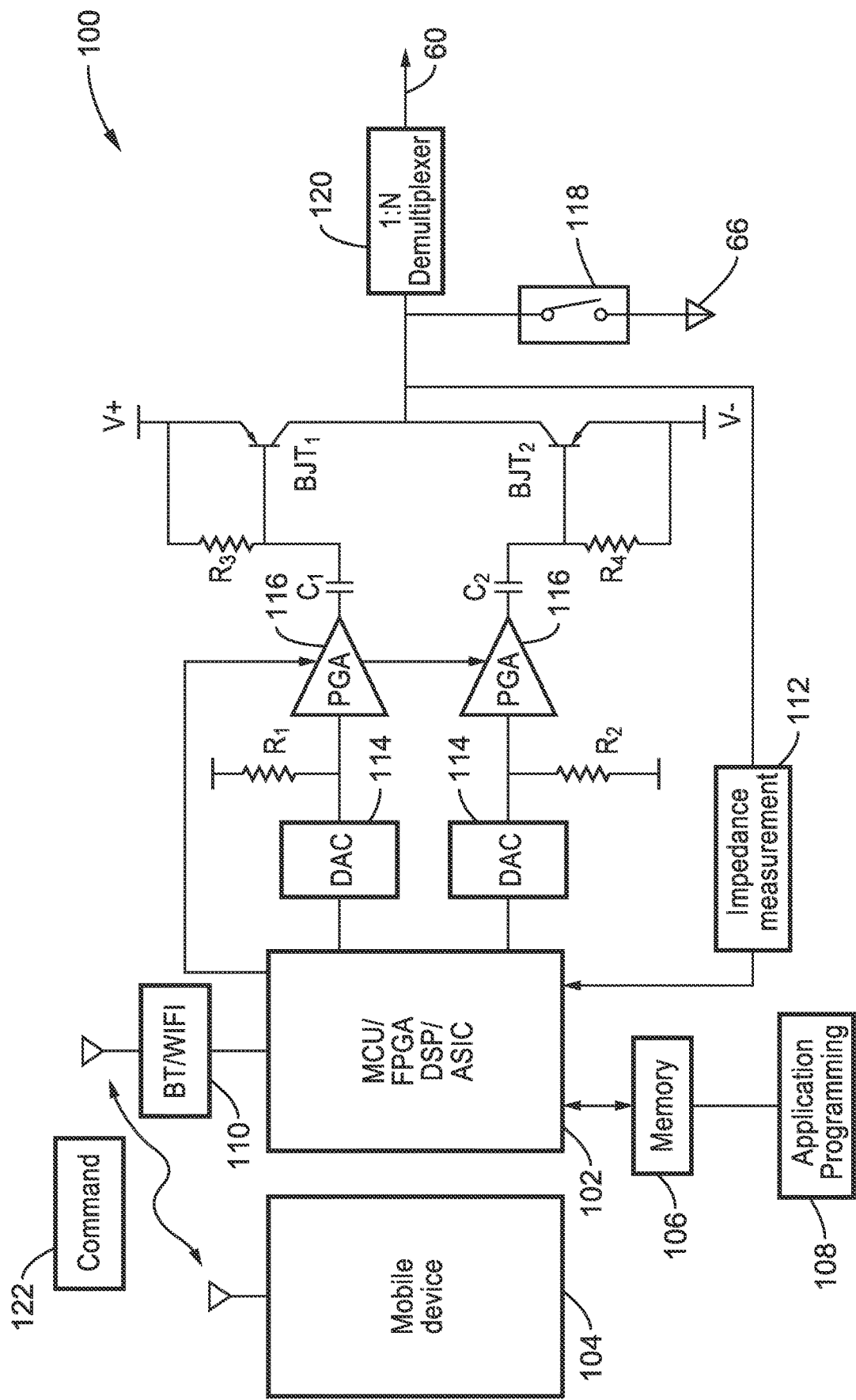

FIG. 11 is a schematic block diagram of a non-invasive stimulator in accordance with the present description.

Figure 12:
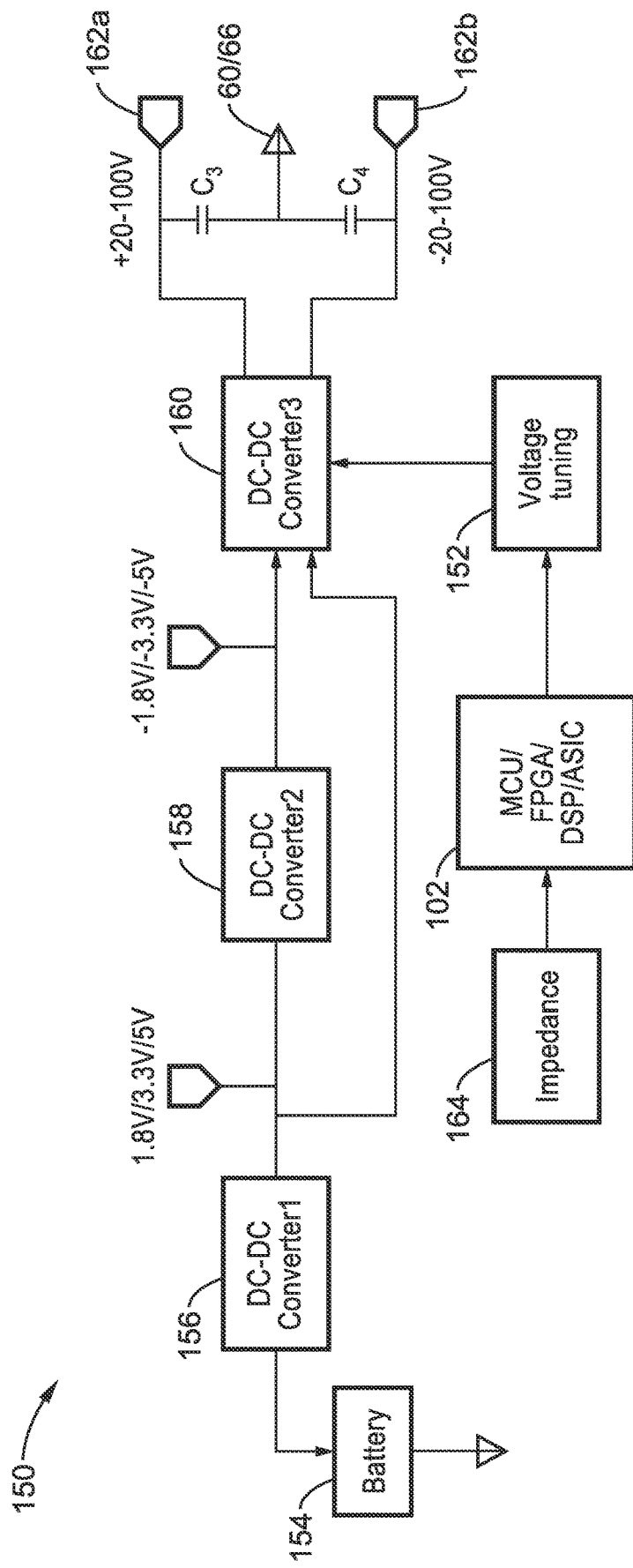

FIG. 12 is a schematic block diagram of the power management circuit for the stimulator of FIG. 11.

DETAILED DESCRIPTION

A first aspect of the technology described herein is based on systems and methods for implementation of a disposable miniaturized implant for treatment of treating gastrointestinal dysmotility, including dysphagia, gastroesophageal reflux disease (GERD), nausea, functional dyspepsia, blockage of transit, and obstruction of the GI tract (e.g., gastroparesis, post-operative ileus, inflammatory bowel diseases). One function of the implant is to provide electrical stimulation to the GI tract through direct stimulation on enteric nervous system/ICCs or the cercial and celiac branches of the vagus nerve. A second function of the implant is to provide electrical stimulation to the part of bowel going through surgery to expedite the healing process while recording the smooth muscle activities simultaneously; the third function of the implant is to reduce regulating GI motility through intestinal electrical stimulation for treating obesity. A fourth function of the implant is to record the pH value, pressure, transits time. Disposability of the implant is a key feature, as patients with POI would be less willing to undergo anther surgery to remove the device. For other chronic disease, the device would be a permanent implant.

A second aspect of the technology described herein is based on systems and methods for non-invasive, transcutaneous stimulation of anatomy within the abdomen of the patient.

A. Disposable Gastrointestinal Stimulator

Figure 1:
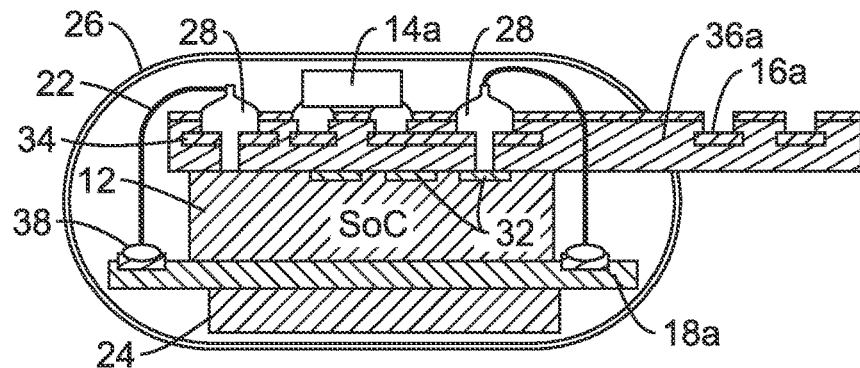
FIG. 1 shows a schematic side view of the gastrointestinal (GI) stimulation implant of the present description.
Figure 2:
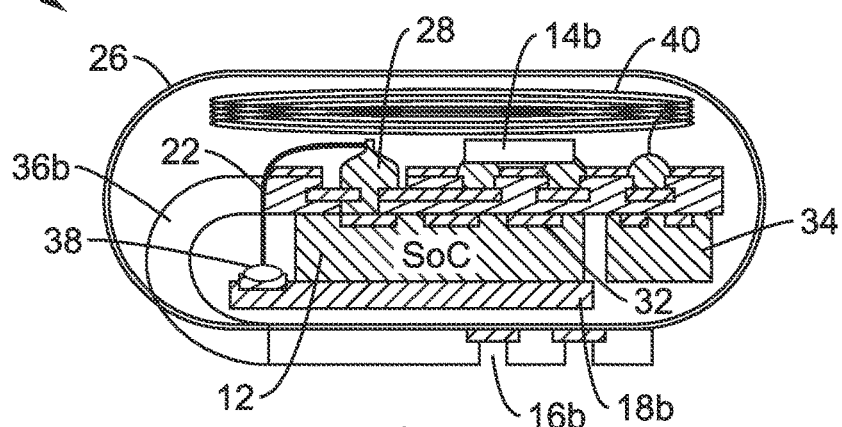
FIG. 2 shows a schematic side view of an alternative GI stimulation implant.
Figure 3:
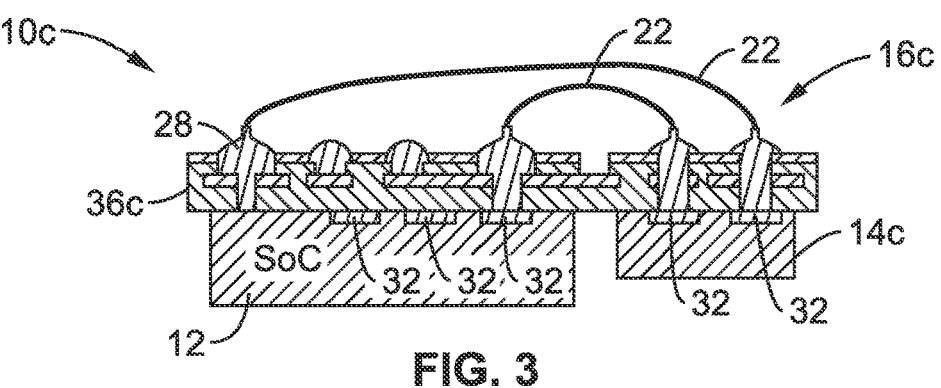
FIG. 3 shows a schematic side view of an alternative GI stimulation implant.

FIG. 1 through FIG. 3 show schematic side view of three different gastrointestinal (GI) stimulation implants (10a through 10c, respectively) in accordance with the present description. GI stimulation implants 10a through 10c preferably comprise disposable GI implants that are battery powered (preferably with a rechargeable battery) to perform current mode stimulation. The GI stimulation implants 10a through 10c are implemented by heterogeneously integrating the microelectronics (i.e., the system-on-a-chip SoC), the battery, the antenna, other passive/active surface mounted components, and the electrode array into a single biocompatible package. In a preferred embodiment, the GI stimulation implants 10a through 10c electrically modulate the gastrointestinal tract smooth muscles and the neurons residing in the muscularis externa to restore GI motility and inflammatory responses, as well as wirelessly record the GI motility by measuring the electrode-tissue impedance, pH value, transit time, and pressure. In another embodiment, the implants 10a through 10c are configured to electrically modulate the vagus nerve to regulate autonomic functions.

FIG. 1 illustrates a first configuration of a GI implant 10a having a battery 24 placed on the bottom side of the printed circuit board (PCB) interposer 18a. In this embodiment, the PCB interposer 18a is also used as an antenna for wireless signal transmission and recording. A substrate 36a comprising an electrode array 16a is provided for delivering GI stimulation. Electrode array 16a may also be configured as a cuff electrode (not shown) for nerve stimulation. In a preferred embodiment, the substrate 36a comprises a flexible material, such as polyimide, parylene, silicone, or PDMS, or the like, with a thickness generally ranging from 5 um to 50 um. The flexible substrate 36a also serves as a soft interposer board in which electrical connections are made by deposition of metal bumps 28 (e.g., Pt, Pt black, Titanium, gold, etc.) at pads 34.

An SoC 12 is positioned underneath the flexible substrate 36a such that specified openings (e.g., round shape or square shape openings) disposed through the flexible substrate 36a expose the metal pads 32 of the SoC 12 to the metallic bumps 28 other passive/active components 14a. The openings on the substrate 36a are aligned to the metal pads 32 of the SoC enable its operation. In one embodiment, Gold/alumina bumps 28 with a diameter from about 20 μm to about 50 μm are positioned on top of the opening to link the SoC 12 and the flexible substrate 36a.

The SoC 12 sits on top of a PCB interposer 18a, which has patterned metal to serve as an antenna and an interposer for the connection with the battery 24. The connection of the PCB interposer 18a to the wireless transmitter/receiver in the SoC 12 is made by wire bonding 22 to pads 38. The use of PCB is important because the flexible substrate 36a has a higher signal loss and its thin metal trace usually results in high resistivity, not suitable for relaying high frequency and weak electrical signal.

In a preferred embodiment, the all or a portion of the stimulation implant 10a is encapsulated in a capsule 26 comprising a biocompatible material (i.e. silicone, PDMS, glass, titanium, ceramic, and epoxy), which may be similar to the shape to a medicine capsule.

FIG. 2 illustrates an alternative configuration of a GI implant 10b having the battery, passive and active components (collectively 14b) integrated with or adjacent to the SoC 12 on the same side or bottom side of the flexible substrate 36b. In this configuration, the resistance of the metal traces on the flexible substrate 36b are taken into consideration.

A PCB antenna 18b is disposed for wireless signal transmission and recording. Substrate 36b comprising an electrode array 16b is provided for delivering GI stimulation. In a preferred embodiment, the substrate 36b comprises a flexible material, such as polyimide, parylene, silicone, or PDMS, or the like, with a thickness generally ranging from 5 um to 50 um. The flexible substrate 36b also serves as a soft interposer board in which electrical connections are made by deposition of metal bumps 28 (e.g., Pt, Pt black, Titanium, gold, etc.) at pads 34. An SoC 12 is positioned on a bottom surface of the flexible substrate 36b such that specified openings (e.g., round shape or square shape openings) disposed through the flexible substrate 36b expose the metal pads 32 of the SoC 12 to the metallic bumps 28 or other passive/active components 14b. The openings on the substrate 36b are aligned to the metal pads 32 of the SoC enable its operation. In one embodiment, Gold/alumina bumps 28 with a diameter from 20-50 μm are positioned on top of the opening to link the SoC 12 and the flexible substrate 36b.

The SoC 12 sits on top of a PCB antenna 18b, which has patterned metal to serve as an antenna and for the connection with the battery in components package 14b. The connection of the PCB antenna 18b to the SoC 12 is made by wire bonding 22 to pad 38.

In a preferred embodiment, the all or a portion of the stimulation implant 10b is encapsulated in a capsule 26 comprising a biocompatible material (e.g., silicone, PDMS, glass, ceramic, titanium, epoxy, or like material), which may be similar to the shape to a medicine capsule.

The GI/nerve implant 10b also comprises one or more implant coils/wire antenna 40. The implantable coils 40 are preferably configured to couple an external device or controller (not shown) via a wireless inductive coupling such that one or more of power and commands may be transmitted to/from the external device to apply a stimulus voltage at a treatment location in a body tissue. In one embodiment (not shown), the inductive coupling is achieved through a power and stimulator module and reverse telemetry module connected to the implant coil. Wherein the implant coil is inductively coupled to an external power coil that is configured to send a power signal to said implant coil, as well as send control stimulation parameters and process reverse telemetry.

As shown in FIG. 2, the flexible substrate 36b is folded over (in a U-shape to wrap around below the SoC 12 and components 14b, and has an embedded array of electrodes 16b directed downward from the device.

Referring now to FIG. 3, an alternative configuration of a GI implant 10c is illustrated that is similar to the embodiment of FIG. 2 except that the flexible substrate 36c upon which the electrode array 16c is disposed is laid straight depending on the needs of different clinical applications.

For critical connections, such as power, ground connection and high frequency signal input/output, bonding wires 22 are used to form the electrical connection, in addition to using the metal trace on the flexible substrate 36c, for the purpose of minimizing the parasitic resistance/capacitance contributed by the flexible substrate 36c.

In a preferred embodiment, the substrate 36c comprises a flexible material, such as polyimide, parylene, silicone, or PDMS, or the like, with a thickness generally ranging from 5 um to 50 um. The flexible substrate 36c also serves as a soft interposer board in which electrical connections are made by deposition of metal bumps 28 (e.g., Pt, Pt black, Titanium, gold, etc.) at pads 34. An SoC 12 is positioned on a bottom surface of the flexible substrate 36c such that specified openings (e.g., round shape or square shape openings) disposed through the flexible substrate 36c expose the metal pads 32 of the SoC 12 and/or other passive/active components 14c (which may also comprise a battery and/or antenna) to the metallic bumps 28. The openings on the substrate 36c are aligned to the metal pads 32 of the SoC 12 and components 14c to enable their operation. In one embodiment, Gold/alumina bumps 28 with a diameter from 20-50 μm are positioned on top of the openings to link the SoC 12 and components 14c and the flexible substrate 36c.

Figure 5:
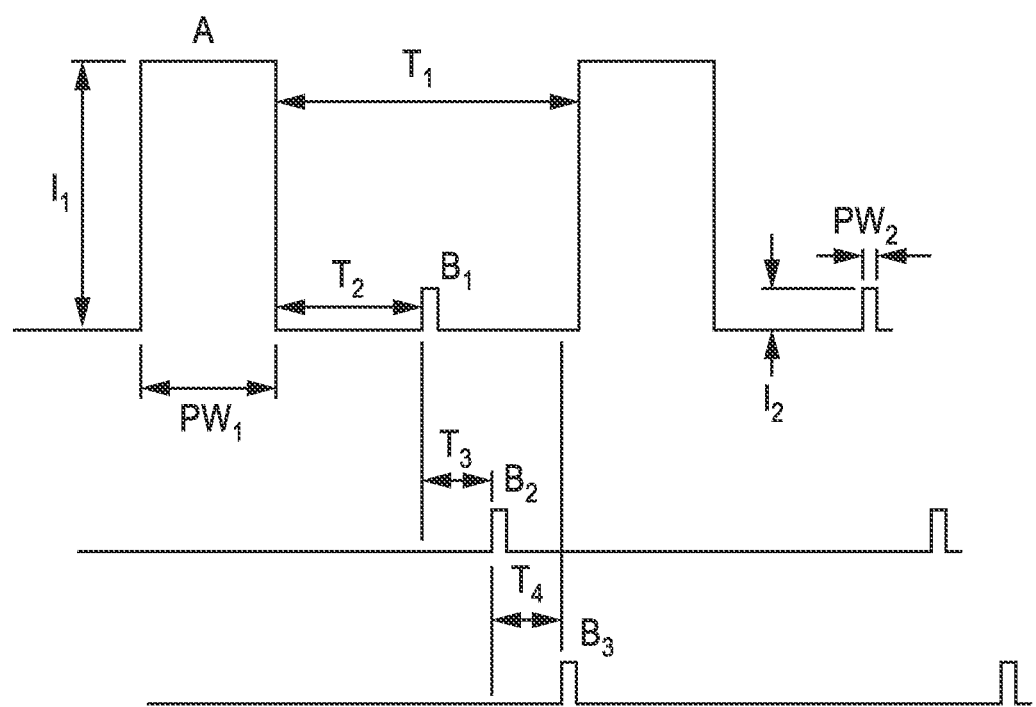
FIG. 5 is an image of a stimulation waveform for triggering muscle/neuron response and impedance/motility measurements in accordance with the present description.
Figure 6:
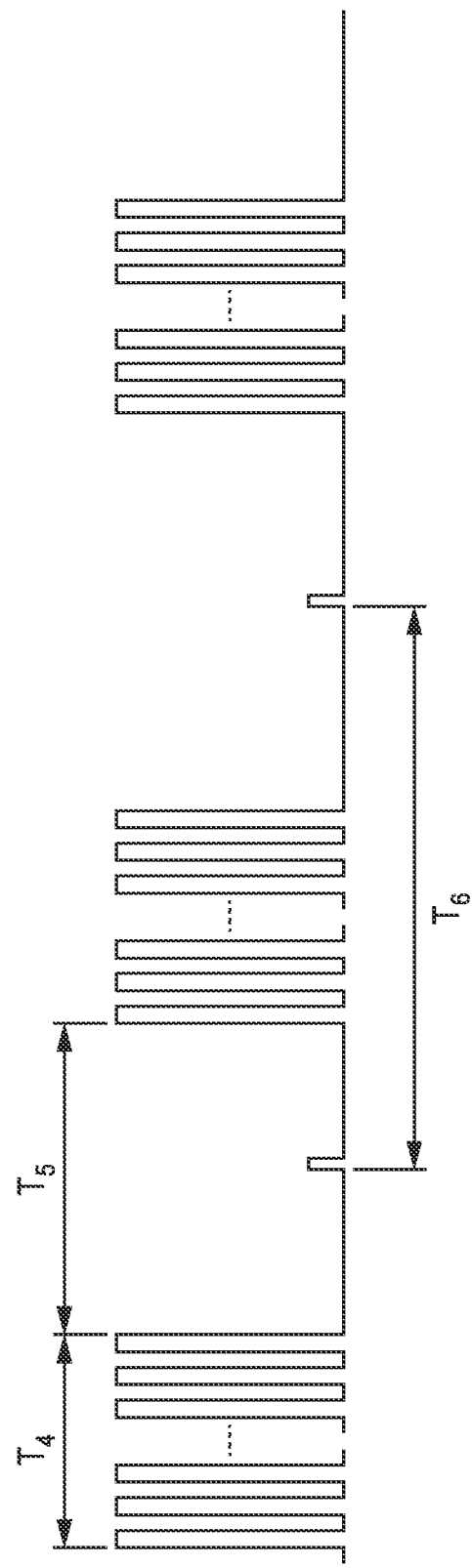
FIG. 6 is an image of grouped stimuli for triggering muscle/neuron response and impedance/motility measurement in accordance with the present description.

One or more of the SoC and active/passive components comprise application programming and a processor for activating the electrode array 16 according to a stimulation waveform as shown in FIG. 5 or 6, discussed in more detail below.

Figure 4A:
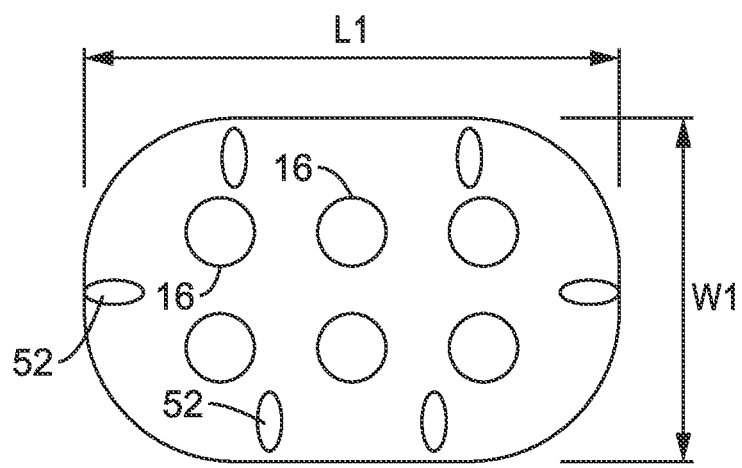
FIG. 4A through FIG. 4C show bottom views of an intraluminal device with varying electrode configurations.
Figure 4B:
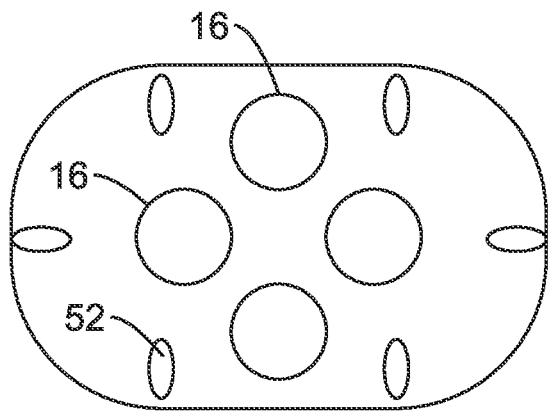
Figure 4C:
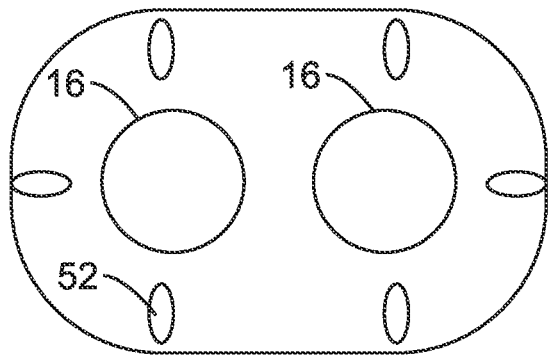

FIG. 4A through FIG. 4C show the bottom views of the intraluminal electrode arrays (50a through 50c, respectively). So that the gastrointestinal tract is not obstructed, electrode arrays 50a through 50c preferably have footprints such that length (L1) and width (W1) and height (into page) are configured to be less than about 1 cm. Sutures holes 52 may be provided through the substrate, and in one configuration the suture holes 52 are distributed on four sides of the electrode array 50a, 50b, and 50c to allow clinicians purchase for anchoring the device inside the GI tract or the nerve through a buckle (not shown). For the application of transient GI implant for POI, the size of the suture holes 52 is generally in the range of 0.05 to 0.7 mm, allowing the use of synthetic absorbable/biodegradable suture wires (not shown) with different gauges. The absorbable/biodegradable suture wires are configured to dissolve after a period of time, thus allowing the implant to pass out of the GI tract without surgery for removal.

The number of electrodes 16 may vary from the simplest configuration of two electrodes in the array 50a of FIG. 4A to the four-electrode array 50b of FIG. 4B, six-electrode array 50c of FIG. 4C, as well as any number of electrodes, or even a cuff electrode for nerve stimulation and recording. In the two-electrode configuration 50a of FIG. 4A, one electrode serves as the stimulation/recording electrode and the other one is the return/ground electrode or vice versa.

In a preferred embodiment, each of the electrodes in the array 50a through 50c are individually addressable for stimulation at distinct timing, frequency, or power.

The size of the electrodes 16 preferably ranges to be below 9 mm$^2$ (e.g., 3 mm×3 mm) with a spacing of <2 mm. In the electrode array configuration, the size of each electrode is set to <2 mm$^2$ with a spacing of <2 mm. Each electrode 16 can be configured as ground/return, stimulation, recording, or concurrent stimulation and recording electrode. Multiple electrodes 16 can be used to deliver stimulus simultaneously with different parameters. The material of the electrode 16 can be silver, gold, platinum, titanium, or alloys. The electrode shape can also be strip, instead of round shape as shown, to ensure the device can interface with the biological tissue, regardless of its displacement. In one embodiment, pH sensing material may be coated on the electrode 16 for pH measurement.

FIG. 5 shows one configuration of the current stimulation waveforms that may be delivered from any of the electrodes 16 or electrode arrays in the intraluminal implants detailed above. It is appreciated that while a single polarity stimulus is shown in FIG. 5 for the purpose of illustration, the stimulus may also be a biphasic stimulus (i.e. either cathodic first and anodic first), or other form know to one of skill in the art. Stimulus A is a high intensity pulse used to trigger the muscle/neurons. Its pulse width, PW1, is configured to be in the range of 0.5 ms-100 ms, with intensity from 0.5 mA to 10 mA. The stimulation frequency, $1/T_1$, is preferably set from 0.01 Hz to 300 Hz. A low intensity short stimulus, $B_1$, is inserted between each strong stimulus. Stimulus $B_1$ should be issued after the electrode overpotential is back to its baseline value after the perturbation of stimulus A. The separation between stimuli A and $B_1$ (i.e., $T_2$) can be more precisely determined based on the electrode-tissue impedance.

In one embodiment, the purpose of stimulus $B_1$ is to monitor the tissue impedance during the contraction and/or relaxation of the GI smooth muscle. Tissue impedance is derived by measuring the electrode overpotential evoked by stimulus $B_1$. The pulse width of stimulus $B_1$ can be set in the range of 10 µs to 1000 µs, based on the size of the electrode 16 (i.e., impedance of the electrode used) such that the delivered current (i.e., electric charge) flows to the tissue through the non-faradic reaction via the double layer capacitance of the electrode-tissue interface. Under such, the varying tissue impedance can be simply acquired by measuring the peak evoked electrode overpotential resulting from stimulus B and the known stimulation intensity. The intensity should be set to a range in order to ensure that the evoked electrode overpotential does not saturate the signal-recording circuit of the implant. Stimulation intensity used in our proof-of-concept experiment is from <1 µA to 1 mA.

In order to measure the GI propagation wave during smooth muscle contraction and/or relaxation, multiple electrodes can be used for GI impedance/motility recording. This is done by employing other electrodes to deliver low-intensity stimuli (e.g., $B_2$ and $B_3$) and carefully assigned a firing timing offset (i.e., $T_2$-$T_4$#0). If $B_{1-3}$ have different polarity than the stimulus A, firing timing of $B_{1-3}$ needs to be offset from that of stimulus A to ensure that the current contributed by $B_{1-3}$ does not flow directly to the electrode that delivers stimulus A, affecting the accuracy of the impedance/motility measurement.

Because stimuli $B_1$-$B_3$ are not designed to fire simultaneously, special consideration must be taken to determine the minimum delays between each stimulus. This is important, as many stimulators adopt passive charge to remove its residual charge by shorting the electrodes to the ground/reference electrode after each stimulation. It is therefore possible that during the firing of $B_1$ the injected current would simply flow to the adjacent electrode configured to fire $B_2$, if it happens to perform passive discharge. The firing delay of stimuli for impedance/motility measurement (e.g., $T_2$, and $T_3$) can be determined based on the discharging time estimated by deriving the impedance of electrode-tissue interface. At least, $T_1$-$T_3$ should be set at least 2 times the value of $PW_2$.

In another embodiment, the delivered stimuli are configured to mimic the nature electrophysiological signals, including one or more of: EMG, EGG, ECG, action potentials, and local-field potentials.

FIG. 6 shows another configuration of stimulation parameters. Several pulses are grouped to trigger the activation of muscle/neurons during the duration of $T_4$. $T_4$ is generally set to the range between 0.5 ms to 60 s, depending on the number of stimulus to be sent. The stimulation frequency, $1/T_5$, generally ranges from 0.01 Hz to 300 Hz. Between each group of stimuli, again, low intensity stimulus is inserted for impedance/motility measurement, in which the firing frequency, $1/T_6$, will ideally be the same as $1/T_5$ to avoid the overlapping of both types of stimuli. The stimulus for impedance measurement can be either a single pulse, a pulse train, a sinusoidal wave, or the like.

B. Non-Invasive Gastrointestinal Stimulator

In addition to performing intraluminal stimulation and motility recording via the implant 10a through 10c shown in FIG. 1 through FIG. 3, non-invasive transcutaneous electrical stimulation may also be employed for gastrointestinal therapeutics.

Figure 7A:
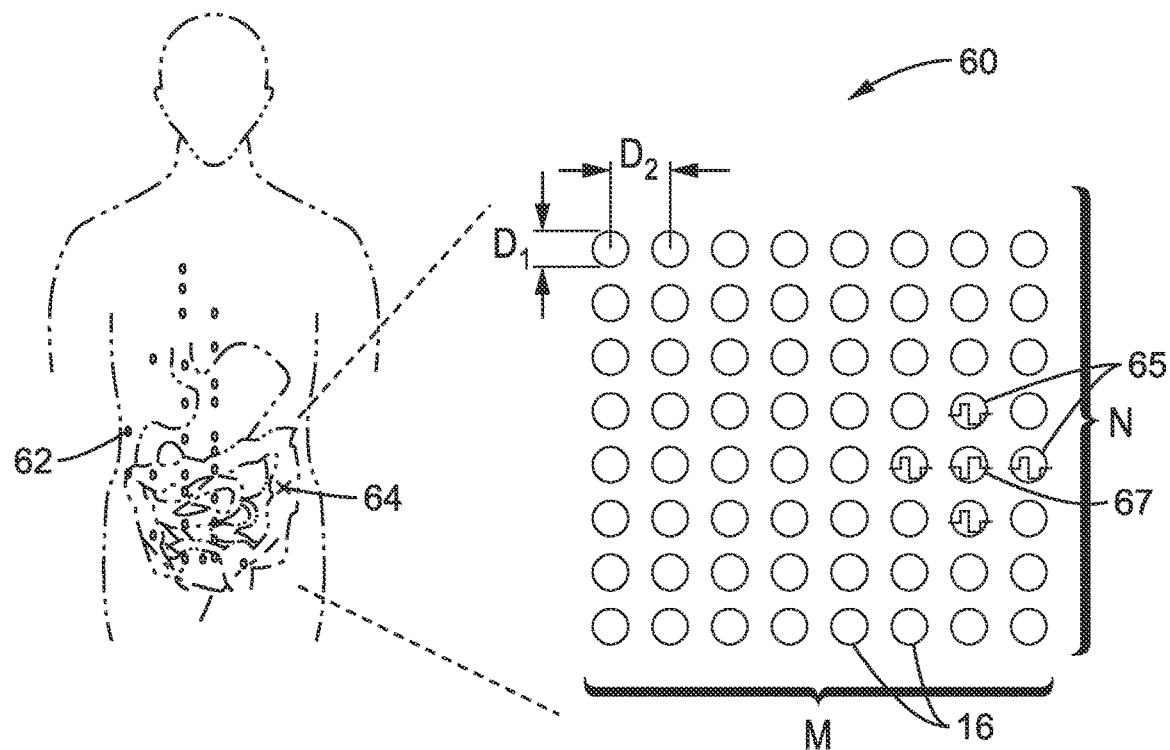
FIG. 7A shows a front view of ventral body anatomy with acupuncture points and the electrode array of the present description.
Figure 7B:
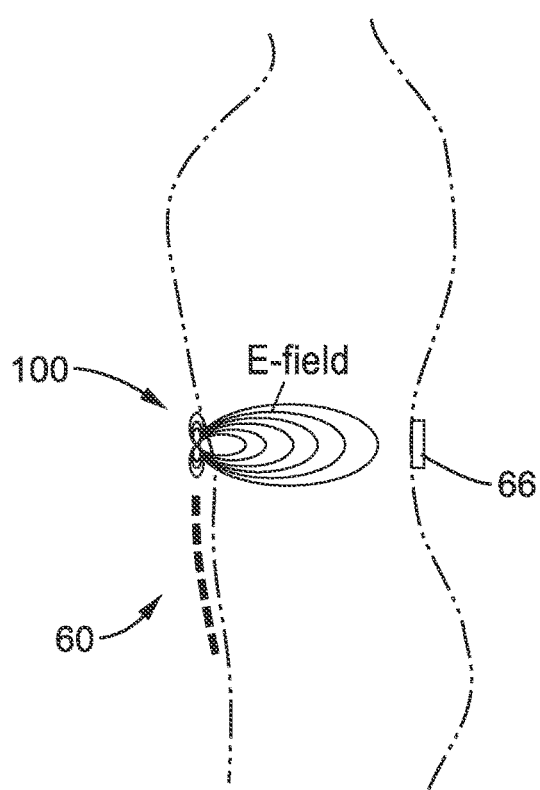
FIG. 7B shows a side view of the patient with the GI stimulation system of the present description.

FIG. 7A shows a front view of ventral body anatomy with acupuncture points and the transcutaneous electrical stimulation array 60 of the present description. FIG. 7B shows a side view of the patient with a transcutaneous GI stimulation system 100 and transcutaneous electrical stimulation array 60 disposed on the abdomen/abdominal wall of a patient in accordance with the present description. Unlike other conventional transcutaneous electrical nerve stimulation (TENS) devices that uses pairs of electrodes to perform bipolar stimulation for pain suppression and simple stimulation strategy/waveform, a multiple electrode array 60 is implemented to allow: 1) the spatial steering of the injected electrical charge to the target locations/tissues of interest within the anatomy; 2) a unique retarded stimulation waveform to minimize the unwanted edge effect during stimulation; and 3) electrode structures that not only lower the electrode-tissue interface impedance, but also avoid the influence of sweat that might create direct short circuit between two adjacent electrodes.

Referring to FIG. 7A, the diameter ($D_1$) of the electrodes 16 generally ranges from 5 mm to 50 mm. The spacing ($D_2$) between electrodes generally ranges from 3 mm to 100 mm. The number of electrodes (M by N) may be varied based on the area of the stimulation target region. The electrode array 60 may be directly placed on top of the acupuncture points 62 that govern/facilitate the functionalities of the internal organs (i.e., stomach, intestine, colon, bowel, liver and so on). Each electrode 16 in electrode array 60 is independently addressable for stimulation, and multiple electrodes 16 may be used to deliver stimuli simultaneously with different parameters to shape the resulting electrical field (FIG. 7B) for focused stimulation. Each electrode can also be used to record the electrophysiological signals produced by the GI tract non-invasively.

Thus, stimulation system 100 is not only capable of stimulating the acupuncture points 62, but the stimulation current can be steered and applied to the target inside the body. In one example, if the patient received a surgery and has a surgical cut 64 made on his colon, stimulation current can be delivered from the electrodes on the abdominal wall which is close to the colonic segment undergoing surgery. By deliberately setting the stimulation parameters, the current that would otherwise spread to unwanted (i.e. non-treatment) regions within the body is minimized. In the example shown in FIG. 7A, a cathodic first biphasic stimulus is applied to a center electrode 67, and four adjacent electrodes 65 are given anodic first stimuli concurrent to focalize the stimulation current. More complex current weighting can be applied based on the depth, size, and location of the stimulation site. The duration for continuous stimulation should generally be less than 30 minutes in order to avoid unwanted tissue/neural damage. In another example, the electrode array can be placed on the back of the patient to stimulate the spinal ganglion for the modulating of GI motility and autonomic nervous system.

Referring to FIG. 7B, a return/ground electrode 66 is positioned on the back of the subject opposite the stimulation array 60, or vice versa. In one application, the location of return/ground electrode 66 may be close to the midline or midline of the thoracic, lumbar, and sacral spines, allowing the stimulation current to pass through spinal ganglions where neuron/sympathetic/parasympathetic nerves reside, and then to be collected by the return/ground electrode 66.

With respect to a patient's skin, the stratum corneum (SC) is the outmost part of the skin, with a thickness in the range of 10-40 µm, and is thought to be the main contributor of the skin impedance. Conventional planar electrodes used for stimulation inject current from the high impedance SC layer, and thus inevitably set a requirement of high compliance voltage for the stimulator. For an electrode-tissue impedance of 2 kΩ using a planar electrode, delivering a 100 mA stimulus necessitates a high compliance voltage of 200 V for the stimulator, drastically increasing the its power consumption and possibly resulting in skin burning. Equally important, sweating is a non-negligible concern that needs to be taken into consideration during stimulation. The average density of sweat gland is 200 per square centimeter. The sweat gland resides in the dermis layer, and its duct conveys sweat to the surface of the skin. Excessive sweating may create direct shorting between electrodes or cause the stimulation current to spread to undesired targets.

Figure 8:
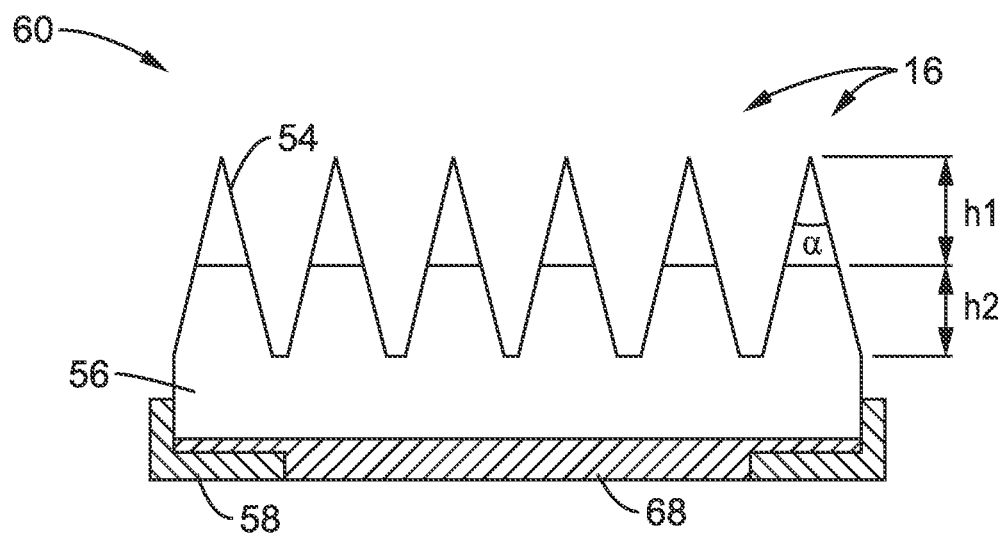
FIG. 8 is an enlarged side view of the electrode structure of the present description.

FIG. 8 is an enlarged side view of the electrode array 60 structure in accordance with the present description. In a preferred embodiment, the electrode array 60 comprises a plurality of conical penetrating spike electrodes 16 array, with only the tips 54 of the spikes exposed. The substrate 56 supporting the electrodes 16, and a lower portion of the spike are preferably electrically insulated, e.g., by coating a lower portion of the spike and substrate 56 with a layer of non-conductive biocompatible material (i.e., epoxy, PDMS, polyimide, parylene, and silicone). The insulation layer ensures excessive sweat will not create shorting between electrodes, especially in the scenario that a high intensity current is used for neuromodulation. The height of the electrode 16 is configured to be larger than the thickness of the SC layer (e.g., 15-140 µm), and pierce the skin to bypass the high-impedance SC layer and the sweat gland. With such configuration, the compliance voltage of the stimulator may be much less stringent. In one example, the height $h_1$ of the exposed tip 54 of each spike on one electrode ranges from 5 µm-100 µm with an angle of α, where α ranges from 5° to 45°. The height of the insulated section ($h_2$) of each spike may be set according to desired protection from electrode 16 shorting. Since the electrode tips 54 are exposed to low-impedance skin layers, under the same intensity of stimulus as conventional planar electrode or spike electrode with no insulation layer, less power is consumed (i.e., Power=Current×Impedance²), and hence less heat is generated for minimizing the possibility of skin burning.

The shape of the electrode substrate 56 is also configured for mitigating the stimulation edge effect, in which the edge of the electrode 16 has the strongest electric field during the onset of electrical stimulation. Edge effect results in uncontrolled strong E-field that possibly damages the tissue/neuron/skin. Thus, unlike widely used circular/square/rectangular electrodes, the electrode substrate 56 presented herein is configured in such a way that its shape is symmetric, but has different path lengths from the center to the edge of the electrode for reducing the edge effect, such as a heptagram and octagram. The array 60 may further comprise an insulated electron holder 58 and conductor 68 that provides transfer of electrical current to the electrons. As shown in the embodiment of FIG. 8, the shown series of six spikes make up one electrode 16.

Figure 9A:
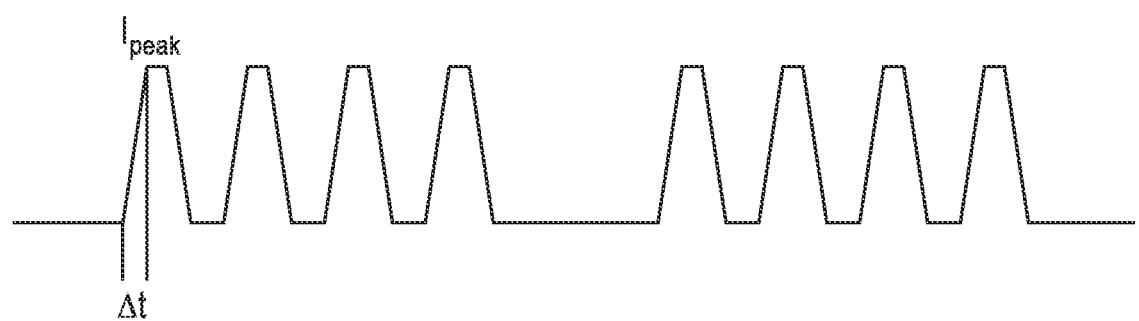
FIG. 9A is an image of a retarded stimulation waveform.

FIG. 9A and FIG. 9B show images of exemplary stimulation waveforms that may be used for stimulating a target region of interest. FIG. 9A shows a retarded stimulation waveform that has been commonly used to reduce the edge effect. In contrast to the square stimulation pulse, a predetermined rising time of the stimulus (Δt) is inserted for injecting a stimulus with the intensity $I_{peak}$. Though this is a method for mitigating edge effect, it imposes stringent hardware specification for the stimulator when high frequency stimulus is required. For example, there are applications that fire 5-10 kHz stimulus (0.1 ms pulse width) in the form of pulse train into the tissue. The purpose of the 5-10 kHz stimulus is reported to block the pain fiber so that the subject does not feel pain during the stimulation. If the retarded waveform has a rising time of $\frac{1}{10}^{th}$ of its pulse width and there are 10 steps increment for the current to go from 0 to $I_{peak}$, the circuits of the stimulator, such as DAC, need to be able to produce its output rate at a minimum of 1 Mbps, possibly increasing the design complexity and performance requirement of the circuit components.

FIG. 9B illustrates a stepwise stimulation waveform using a stepwise pulse train to mitigate the stimulation edge effect in accordance with the present description. Each pulse is either mono-phasic or biphasic stimulus. $I_{peak}$ is the targeted stimulation intensity, which may vary from sub-1 mA to 300 mA. $PW_3$ and $PW_4$ are the pulse widths of each stimulus, which do not need to be equal, (as well as all other pulses in pulse train). In one embodiment, the pulse width varies from 10 µs to 10 ms. $T_{gap}$ is the separation between two consecutive pulses and may vary from 0 to 100 times the pulse width. Again, $T_{gap}$ can vary between each consecutive two pulses. Lastly, $T_{period}$ is the separation between two pulse trains and $1/T_{period}$, is configured to be from sub-1 Hz to 300 Hz. The stimulation waveform is generated by first determining the number of steps N and the peak stimulation current $I_{peak}$. For example, if N=10 and $I_{peak}$ is 100 mA, 9 (i.e. N−1) step-up current pulses would first be generated before reaching 100 mA. Subsequently, based on the user's specification and clinical performance of the subject, a specific number of stimuli with 100 mA intensity are fired. In the end of the pulse train stimulation, corresponding 9 step-down pulses are fired in the reciprocal order of the initial 9 step-up current pulses. When multiple channels are turned on simultaneously, the onset time of each group of pulse train is interleaved to avoid the concurrent firing, meaning $T_{delay}$ should be larger than the length of the pulse train and smaller than $T_{period}$. This arrangement alleviates the design burden of the power management circuits in the stimulator, and avoids the risk of injecting a large current into the subject. In the scenario of DC current stimulation, concurrent firing of multi-channel would limit the overall injected current to <10 mA to avoid tissue/neuron damage.

FIG. 10A through FIG. 10D show various stimulation current injection schemes in accordance with the present description. In addition to stimulating through a specific electrode or a group of electrodes concurrently with different current ratios, the stimuli may be delivered into the electrodes of interests based on an order defined by the clinician/researcher/scientist/patient. The purpose of the ordered stimulation onset is to mimic to physical massage in which muscles are kneaded in a certain order. A subset of examples of the stimulation order is demonstrated in FIG. 10A through FIG. 10D, which show an 8×8 electrode array 60 (for exemplary purposes only). The arrow sign indicates the direction of onset sequence of the stimulation.

FIG. 10A shows stimulated electrodes 70a in an onset sequence of stimulation horizontally from left to the right. Electrodes 72a are not engaged in this sequence.

FIG. 10B shows stimulated electrodes 70b in a diagonal onset sequence of stimulation. Electrodes 72b are not engaged in this sequence.

FIG. 10C shows stimulated electrodes 70c in a clockwise rectangular onset sequence of stimulation. Electrodes 72c are not engaged in this sequence. FIG. 10D shows stimulated electrodes 70d in a clockwise spiral onset sequence of stimulation. Electrodes 72d are not engaged in this sequence.

Multiple electrodes can also be activated to deliver electrical stimuli to through the skin.

It is appreciated the sequences shown in FIG. 10A through FIG. 10D are for illustrative purposes only, and any arrangement or number of sequences may be implemented according to the desired therapy and/or target tissue region.

FIG. 11 shows a schematic block diagram of the non-invasive transcutaneous stimulator system 100 of the present description. The system 100 is configured for use with a mobile device 104 (i.e., cell phone, smart watch, tablet, laptop or like device) to transmit commands 122 to the stimulator through a wireless signal such as Bluetooth or WiFi. The command 122 is received by a wireless circuitry 110 and subsequently processed by a microprocessor 102 (e.g., MCU/FPGA/DSP or a customized application specific integrated chip (ASIC)), and then stored in the memory 106. Based on the received commands, the application programming 108 stored in memory 106 executes instructions related to command 122 via MCU/FPGA/DSP/ASIC 102, which delivers the control signals to the digital-to-analog converters (DACs) 114 to configure the stimulation current. Mobile device 104 may also comprise application programming (in addition to or in place of instructions in programming 108) that contains instructions for providing the command 122 stimulus/stimuli, and associated memory for storing the programming and processor for executing and transmitting command 122.

It is important to point out that conventional stimulator designs adopt current mirrors to amplify the output current of the DAC and to convey the amplified current to the stimulator output stage. If this configuration is implemented using integrated microelectronics, the DAC usually outputs a small current while the current mirror is designated to support high current gain to optimize the power consumption of the electronics at the cost of larger chip area. In contrast, if the stimulator is to be developed using off-the-shelf components, there are generally no off-the-shelf high-gain current mirrors available, and thus inevitably increases the footprint of the stimulator when a high gain ration is desired. Moreover, as a high-compliance voltage is required for the stimulator to accommodate various electrode-tissue impedances and large stimulation current, the adoption of current mirrors further increases the power consumption of the stimulator.

Hence, a viable solution is setting the stimulation current by directly configuring the base/gate voltage of the transistor (e.g., BJT or MOSFET). In the stimulator of FIG. 11, $BJT_1$, and $BJT_2$ form the output stage of the stimulator. $R_3$ and $R_4$, along with the current generated by the PGA outputs, form the base current of the BJTs or the overdrive voltage when MOSFETs are used. V+ and V− are the supply voltage of the stimulator and their value ranges from ±10V to ±100V to support a wide range of stimulation current and various types of electrodes. The base node of the $BJT_{1-2}$ is tied to its emitter through the pull-up resistor, $R_{3-4}$, to ensure there is no output current when the stimulator is set to be off and no command signal is issued. Subsequently, when stimulation is on, the DAC's 114 deliver current or voltage output to the programmable gain amplifiers (PGAs) 116. The (PGAs) 116 can be a voltage- or current-mode amplifier that generate voltage or current outputs. Note that the function of resistor $R_1$ is to convert the output current of the DACs 114 into voltage if a current-mode DAC is adopted. The DACs 114 can also be integrated in the ASIC so that multiple DACs can be incorporated to build a multi-channel stimulator without taking too much space of the stimulator. The gain of the PGA 116 is set based on the desired output current. The PGA 116 then drives the BJT through a high pass filter (HPF) made of $R_{3-4}$ and $C_{1-2}$. The use of the HPF provides the advantage that the DAC/PGA can be powered using low supply voltages (e.g., 1.8V/3.3V/5V) to significantly reduce the overall system power consumption. During the stimulation, the stimulation command is sent preferably using the pulse waveform, e.g., similar to the waveform of FIG. 9B, to the base of the BJT (or the gate of a MOSFET). The amplitude and width of each pulse then results in the intended stimulation current waveform set by the user.

A discharge switch, S1 118, is connected to the stimulator output. Switch 118 is shorted to ground/return electrode 66 at the end of each stimulus to remove the residual charge. The control voltage to the discharge may be set to avoid the undesired turn-on of the discharge switch 118 during stimulation. For example, the control voltage can be either V+ to enable the charge cancellation or V− to disable charge cancellation. A one-to-N output de-multiplexer 120 is also connected to the stimulator output for the purpose of expanding the number of electrodes in array 60 driven by the stimulator.

An impedance measurement circuit 112 is also connected to the stimulator output to measure the electrode-tissue impedance. This measurement can be performed, for example, by injecting a sinusoidal/square current and measuring the evoked electrode bio-potential, or by using the techniques described in PCT International Publication No. WO 2015/168162 published on Nov. 5, 2015 and incorporated herein by reference in its entirety. Measuring impedance can ensure the reliability of the electrode and be used as indicator to dynamically adjust the compliance voltage of the stimulator for power saving. For instance, if the electrode-tissue impedance is 0.5 kohm and a 100 mA stimulus is delivered to the electrode, then the compliance voltage should be set as ±50V. If the stimulation intensity is dropped to 50 mA, the required compliance voltage is only ±25V. Adaptively adjusting the compliance voltage based on the known stimulation intensity and the electrode-tissue impedance can optimize the power efficiency of the stimulator.

The impedance measuring circuit may also measure conductivity between any two electrodes to determine if a short circuit has formed between electrodes and monitor a reparation rate of the patient.

FIG. 12 shows a schematic diagram of a power management circuit 150 to be used with stimulation system 100. Its main function is to generate both high negative and positive supply voltages for the stimulator from a battery 154. The first DC-DC power converter 156 produces 1.8/3.3/5V from the battery 154, and the $2^{nd}$ DC-DC power converter 158 produces −1.8/−3.3/−5V by taking the 1.8/3.3/5V input. The $3^{rd}$ DC-DC power converter 160 subsequently generates both positive and negative high compliance voltages. Capacitors, $C_3$ and $C_4$, are connected to the power converter outputs and share the same common node connected to the ground/return electrode 60/66. The use of $C_{3-4}$ helps define the positive and negative compliance voltages 162a/162b relative to the body potential sensed by the ground/return electrode 60/66. Once the electrode-tissue impedance 164 is known and the stimulation intensity is determined, the MCU/FPGA/DSP/ASIC 102 sends a command to the voltage tuning circuits 152, which may comprise a resistor ladder, to adjust the output of the $3^{rd}$ DC-DC power converter 160.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general-purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing the instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that the present disclosure encompasses multiple embodiments which include, but are not limited to, the following:

1. An implantable apparatus for stimulating a target anatomy, comprising: a flexible substrate configured to house a plurality of electrodes disposed in an electrode array; a system-on-chip (SoC) coupled to the flexible substrate; wherein the SoC is positioned on one side of the flexible substrate such that specified openings disposed through the flexible substrate align with conductive pads of the SoC; and passive/active components coupled to the SoC; wherein the implantable apparatus is configured to be installed at a treatment location of a gastrointestinal (GI) tract of a patient or the vagus nerve and its associated branches; and wherein the electrode array is configured to be activated to electrically modulate and record one or more of GI tract smooth muscles, associated neurons, and nerve fibers to restore GI motility and inflammatory responses within the GI tract.

2. The system, apparatus or method of any preceding or following embodiment, further comprising: a printed circuit board (PCB) antenna coupled to the SoC, the PCB antenna configured to receive signals from an external device for wireless activation of the electrode array and recording of signals from the electrode array; wherein the SoC is disposed between the PCB antenna and the flexible substrate.

3. The system, apparatus or method of any preceding or following embodiment, wherein the PCB antenna acts as an interposer between the SoC and a battery configured to power the apparatus.

4. The system, apparatus or method of any preceding or following embodiment, wherein the flexible substrate wraps around the SoC and PCB antenna.

5. The system, apparatus or method of any preceding or following embodiment, wherein all or a portion of the apparatus is encapsulated in a biocompatible material.

6. The system, apparatus or method of any preceding or following embodiment, wherein the flexible substrate comprises a plurality of suture holes for anchoring the apparatus within the GI tract via an absorbable suture.

7. The system, apparatus or method of any preceding or following embodiment, wherein one or more of the SoC and active/passive components comprise: a processor; a non-transitory memory storing instructions executable by the processor; wherein said instructions, when executed by the processor, perform steps comprising: activating the electrode array according to a user-determined stimulation waveform that is configurable based on the patient's physiological status.

8. The system, apparatus or method of any preceding or following embodiment, wherein the stimulation pattern comprises: a periodic stimulus comprising high-intensity pulses used to trigger muscle or neurons in the GI tract; a low-intensity stimulus comprising a short pulse inserted between each high-intensity stimulus; and wherein the low-intensity stimulus is used to monitor the tissue impedance during a contraction or relaxation of the GI smooth muscle.

9. The system, apparatus or method of any preceding or following embodiment, wherein the tissue impedance is derived by measuring the electrode overpotential evoked by the low-intensity stimulus.

10. The system, apparatus or method of any preceding or following embodiment, wherein said instructions, when executed by the processor, further perform steps comprising: delivering a second low-intensity stimulus via a second electrode in the electrode array separate from a first electrode in the electrode array, the first electrode generating the first low-intensity stimulus; and measuring a GI propagation wave during the smooth muscle contraction/relaxation.

11. The system, apparatus or method of any preceding or following embodiment, wherein the low-intensity stimulus pulse is inserted between a group of at least two high-intensity stimulus pulses.

12. A method for treating post-operative ileus, comprising: installing the disposable implant at a treatment location of a gastrointestinal (GI) tract of a patient; and electrically modulating one or more gastrointestinal tract smooth muscles and associated neurons to restore GI motility and reduce inflammatory responses.

13. The system, apparatus or method of any preceding or following embodiment, further comprising: wirelessly recording the GI motility by measuring one or more of the electrode-tissue impedance, GI pH value, and transit time.

14. The system, apparatus or method of any preceding or following embodiment, further comprising: applying an electrical stimulation at the treatment location at or near a vagus nerve ending to reduce a level of tumor necrosis factor (TNF) associate with the GI tract.

15. The system, apparatus or method of any preceding or following embodiment, wherein modulating is performed by activating the electrode array according to a user defined stimulation pulse waveform that is further adjustable based on the patient's physiological feedback to optimize treatment efficacy.

16. The system, apparatus or method of any preceding or following embodiment, wherein the stimulation pulse waveform is generated via one of more commands sent wirelessly to the implant from a device external to the patient.

17. The system, apparatus or method of any preceding or following embodiment, wherein the stimulation waveform is configured for simultaneous GI stimulation and motility recording, and comprises: a periodic stimulus comprising high-intensity pulses used to trigger muscle or neurons in the GI tract; a low-intensity stimulus comprising a short pulse inserted between each high-intensity stimulus; and wherein the low-intensity stimulus is used to monitor the tissue impedance during a contraction or relaxation of the GI smooth muscle.

18. The system, apparatus or method of any preceding or following embodiment, wherein the tissue impedance is derived by measuring the electrode overpotential evoked by the low-intensity stimulus.

19. The system, apparatus or method of any preceding or following embodiment, the method further comprising; delivering a second low-intensity stimulus via a second electrode in the electrode array separate from a first electrode in the electrode array, the first electrode generating the first low-intensity stimulus; and measuring a GI propagation wave during the smooth muscle contraction/relaxation.

20. The system, apparatus or method of any preceding or following embodiment, wherein the low-intensity stimulus pulse is inserted between a group of high intensity stimulus pulses.

21. A system for stimulating a target tissue of a patient, comprising: (a) a stimulator comprising an array of electrodes configured to transcutaneously deliver an electric field into the target tissue from a first surface on the patient, each electrode the array being independently addressable for stimulation at distinct timing or frequency; (b) a return electrode configured to be positioned on a second surface of the patient opposite the target tissue from the first surface; (c) a processor; (d) a non-transitory memory storing instructions executable by the processor; (e) wherein said instructions, when executed by the processor, perform steps comprising: (i) delivering stimuli to the array of electrodes such that the array simultaneously with different stimulation parameters; and (ii) emitting a shaped and focused electrical field from the array into the target tissue for stimulation of the target tissue; (iii) wherein at least two of the electrodes in the array are sequentially activated with a specified timing so as to generate the shaped and focused electrical field.

22. The system, apparatus or method of any preceding or following embodiment, wherein said delivering stimuli to the array comprises: applying a cathodic biphasic stimulus to a center electrode; and applying an anodic biphasic stimulus to four electrodes adjacent to the center electrode.

23. The system, apparatus or method of any preceding or following embodiment, further comprising: a mobile device wirelessly coupled to the stimulator; wherein the command is delivered to the stimulator from the mobile device; and wherein a recorded physiological signal is delivered to the mobile device from the stimulator.

24. The system, apparatus or method of any preceding or following embodiment: wherein the stimulator is configured to be positioned on an abdominal wall or back surface of the patient; and wherein the return electrode is configured to be positioned on a surface opposite the abdomen of the patient from the stimulator such that the shaped and focused electrical field is directed through the abdomen to be collected by the return electrode.

25. The system, apparatus or method of any preceding or following embodiment, wherein the shaped and focused electrical field is directed through spinal ganglions where neurons, sympathetic, or parasympathetic nerves.

26. The system, apparatus or method of any preceding or following embodiment, wherein the stimuli are delivered as a stepwise stimulation waveform comprising a plurality of spaced apart stepwise pulse trains configured to mitigate the stimulation edge effect.

27. The system, apparatus or method of any preceding or following embodiment, wherein each stepwise pulse train comprises: a series of step-up stimulation pulses each having a current that incrementally increases until a specified peak stimulation current is achieved; one or more subsequent peak intensity pulses at the peak stimulation current; and a series of step-down stimulation pulses each having a current that incrementally decreases.

28. The system, apparatus or method of any preceding or following embodiment, wherein the number of step-up stimulation pulses matches the number of step-down stimulation pulses.

29. The system, apparatus or method of any preceding or following embodiment: wherein two or more electrodes are activated simultaneously; and wherein the onset time of the stepwise pulse train delivered to each electrode is interleaved to avoid the concurrent firing of stepwise pulse trains in separate electrodes to ensure the overall stimulation current does not exceed a safe stimulation limit.

30. The system, apparatus or method of any preceding or following embodiment, wherein the electrode array comprises: a plurality of conical spikes each having an electrically insulated portion and a non-insulated tip; wherein the non-insulated tip has a shape and height configured to penetrate the patient's skin to bypass one or more of or sweat gland of the patient's skin.

31. The system, apparatus or method of any preceding or following embodiment, wherein stimulator comprises: a processor; one or more digital-to-analog converters (DACs) coupled to the processor; and an output stage comprising one or more transistors; wherein the stimulation current of the stimuli delivered to the electrodes is directly configured as a function of base/gate voltage of the one or more transistors.

32. The system, apparatus or method of any preceding or following embodiment, further comprising: one or more programmable gain amplifiers (PGAs) coupled to the one or more DACs; and a high pass filter coupled to the output stage; wherein the current or voltage output are delivered between the one or more DACs and the one or more PGAs to drive the one or more transistors of the output stage through the high pass filter (HPF).

33. The system, apparatus or method of any preceding or following embodiment, further comprising: a discharge switch coupled to an output of the stimulator and the return electrode; wherein discharge switch is shorted to return electrode at an end of each stimulus or group of stimuli to remove any residual charge when necessary.

34. The system, apparatus or method of any preceding or following embodiment, further comprising: an impedance measurement circuit coupled to an output of the stimulator; wherein said instructions, when executed by the processor, further perform steps comprising: (iv) measuring an electrode-tissue impedance; and (v) adaptively adjusting a compliance voltage of the stimulator as a function of a known stimulation intensity and the measured electrode-tissue.

35. The system, apparatus or method of any preceding or following embodiment, wherein said instructions, when executed by the processor, further perform steps comprising: (vi) measuring conductivity between any two electrodes to determine if a short circuit has formed between electrodes.

36. The system, apparatus or method of any preceding or following embodiment, wherein said instructions, when executed by the processor, further perform steps comprising: (vi) monitoring a reparation rate of the patient from the measured electrode-tissue impedance.

37. The system, apparatus or method of any preceding or following embodiment, wherein measuring an electrode-tissue impedance comprises injecting a sinusoidal or square current into the target tissue and measuring an evoked electrode bio-potential.

38. The system, apparatus or method of any preceding or following embodiment, further comprising: a battery coupled to the stimulator; and wherein the stimulator comprises a power management circuit configured to generate both high negative and positive supply voltages from the battery.

39. The system, apparatus or method of any preceding or following embodiment, wherein the power management circuit comprises: a first DC-DC power converter that is configured to produce a first voltage from the battery; a second DC-DC power converter that is configured to produce a second voltage; and a third DC-DC power converter that generates positive and negative high compliance voltages from the first and second voltages.

40. The system, apparatus or method of any preceding or following embodiment, wherein the delivered stimuli are configured to mimic the nature electrophysiological signals, including one or more of: EMG, EGG, ECG, action potentials, and local-field potentials.

41. An implantable apparatus for stimulating tissue, comprising: an implantable coil; a power and stimulator module connected to the implantable coil; a voltage stimulus electrode connected to the power and stimulator module; a reverse telemetry module connected to the implantable coil; a sensor connected to the reverse telemetry module; and a recording electrode connected to the sensor; wherein the implantable coil is configured to couple an external device via a wireless inductive coupling such that the power and stimulator module receives power and commands from the external device to apply a stimulus voltage at a treatment location in a body tissue through the voltage stimulus electrode; wherein the sensor is configured to receive one or more of a stimulus intensity applied by the stimulator module and a physiological signal received from the body tissue; and wherein the physiological signal is transmitted to the external device through wireless inductive coupling.

42. A system for stimulating tissue, comprising: (a) an implantable apparatus; (b) an external device; (c) the implantable apparatus comprising: (i) an implantable coil/antenna; (ii) a power and stimulator module connected to the implantable coil/antenna; (iii) a voltage stimulus electrode connected to the power and stimulator module; (iv) a reverse telemetry module connected to the implantable coil/antenna; (v) a sensor connected to the reverse telemetry module; and (vi) a recording electrode connected to the sensor; (vii) a battery powering the device); (d) the external device comprising: (i) an external power coil; (ii) a power transmitter connected to the external power coil and configured to send a power signal to said implantable coil; and (iii) a controller connected to the external power coil and configured to control stimulation parameters and process reverse telemetry of the implantable apparatus.

43. The system of any preceding embodiment: wherein the implantable apparatus is configured to couple to the external device via a wireless inductive coupling such that the power and stimulator module receives power and commands from the external device to apply a stimulus voltage at a treatment location in a body tissue through the voltage stimulus electrode; and wherein the sensor is configured to receive one or more of a stimulus intensity applied by the stimulator module and a physiological signal received from the body tissue.

44. The system, apparatus or method of any preceding or following embodiment: wherein the wireless inductive coupling comprises a modulated power signal; and wherein transmitted data is inserted at the end of the power signal.

45. The system, apparatus or method of any preceding or following embodiment, wherein the stimulus voltage is configured by modifying a base/gate voltage of a transistor of an output stage of the power and stimulator module 46. The system, apparatus or method of any preceding or following embodiment, wherein the commands from the external device comprises a stimulation command sent using the pulse waveform.

47. A method for treating post-operative ileus, comprising: installing the disposable implant of any of the preceding embodiments at a treatment location of a gastrointestinal (GI) tract of a patient; and applying an electrical stimulation at the treatment location at or near a vagus nerve ending to reduce a level of tumor necrosis factor (TNF) associate with the GI tract.

48. A method treating GI dysmotility and inflammation, comprising installing the implant of any of the preceding embodiments at a treatment location of a gastrointestinal (GI) tract or vagus nerve and its branches of a patient; and applying an electrical stimulation at the treatment location at or near a vagus nerve ending to reduce a level of tumor necrosis factor (TNF) associate with the GI tract or activating smooth muscle activities.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A system comprising:
    a stimulator comprising an array of independently addressable electrodes configured to be positioned on a patient's skin, each electrode of the array of electrodes is configured for transcutaneous stimulation and two or more electrodes of the array of electrodes are activated simultaneously;
    at least one return electrode; and
    a controller comprising:
        a non-transitory memory storing instructions; and
        a processor configured to access the non-transitory memory and to execute the instructions to at least:
            deliver an electrical waveform with a set of stimulation parameters to one or more independently addressable electrodes in the array of electrodes; and
            deliver another electrical waveform with another set of stimulation parameters to one or more other independently addressable electrodes in the array of electrodes,
        wherein the stimulator is configured to emit a shaped and focused electrical field for stimulation of a target tissue based on the electrical waveform and the other electrical waveform, wherein the electrical waveform and/or the other electrical waveform comprises a plurality of spaced apart stepwise pulse trains configured to mitigate a stimulation edge effect, wherein each stepwise pulse train of the plurality of spaced apart stepwise pulse trains comprises:
            a series of step-up stimulation pulses each having a current that incrementally increases until a specified peak stimulation current is achieved;
            one or more subsequent peak intensity pulses at the peak stimulation current; and
            a series of step-down stimulation pulses each having a current that incrementally decreases, and
        wherein an onset time of each of the stepwise pulse trains of the plurality of spaced apart stepwise pulse trains delivered to each of the one or more independently addressable electrodes is interleaved to avoid the concurrent firing of the stepwise pulse trains in separate electrodes to ensure the overall stimulation current does not exceed a safe stimulation limit.

2. The system of claim 1, wherein the instructions to deliver an electrical waveform with a set of stimulation parameters to the one or more independently addressable electrodes in the array of electrodes and the other electrical waveform with the other set of stimulation parameters to the one or more other independently addressable electrodes of the array of electrodes further comprises instructions to:
    apply a biphasic electrical waveform to a center electrode of the array of electrodes; and
    simultaneously apply a biphasic electrical waveform of opposite polarity to four electrodes of the array of electrodes that are adjacent to the center electrode of the array of electrodes.

3. The system of claim 1, wherein the controller comprises a mobile device;

wherein the mobile device delivers the instructions to the stimulator; and
wherein the mobile device is configured to receive a recorded physiological signal from the one or more electrodes of the array of electrodes.

4. The system of claim 1:
wherein the array of electrodes is configured to be positioned on the patient's skin above an abdominal wall of the patient or on a back of the patient; and
wherein the at least one return electrode is configured to be positioned on the patient's skin opposite the abdomen of the patient from the stimulator so that the shaped and focused electrical field is directed through the abdomen to be collected by the return electrode.

5. The system of claim 1, wherein the shaped and focused electrical field is directed through spinal ganglions for the purpose of modulating spinal neurons, sympathetic nerves, or parasympathetic nerves.

6. The system of claim 1, further comprising:
a battery coupled to the stimulator; and
wherein the stimulator comprises a power management circuit.

7. The system of claim 6, wherein the power management circuit comprises:
a first DC-DC power converter that is configured to produce a first voltage from the battery;
a second DC-DC power converter that is configured to produce a second voltage; and
a third DC-DC power converter that is configured to generate a third voltage based on the first and second voltages.

8. The system of claim 1, wherein the electrical waveform and the other electrical waveform are configured to mimic one or more natural electrophysiological signals, wherein the one or more natural electrophysiological signals comprise: an electromyography (EMG) signal, an electroencephalogram (EGG) signal, an electrocardiogram (ECG) signal, one or more action potentials, or one or more local-field potentials.

9. The system of claim 1, wherein the shaped and focused electrical field is directed to target an internal organ or nerve within the abdomen.

10. The system of claim 1, wherein the array of electrodes and the at least one return electrode are configured to be positioned proximal to an acupuncture point, wherein the shaped and focused electric field directs stimulation current to pass through at least one nerve proximal to the acupuncture point.

11. The system of claim 1, wherein the processor is further configured to execute the instruction to record an electrophysiological signal produced by the gastrointestinal (GI) tract non-invasively using one or more additional electrodes in the array of electrodes.

12. The system of claim 1, wherein the electrical waveform and/or the other electrical waveform comprise a predetermined rise time to mitigate edge effect.

13. The system of claim 1, wherein the electrical waveform and/or the other electrical waveform are configured to be delivered to the vagus nerve or vagus nerve endings to reduce tumor necrosis factor (TNF) and improve gastrointestinal motility.

14. A system comprising:
a stimulator comprising an array of independently addressable electrodes configured to be positioned on a patient's skin, each electrode of the array of electrodes is configured for transcutaneous stimulation, wherein the array of independently addressable electrodes comprises:
a plurality of conical spikes each having an electrically insulated portion and a non-insulated tip, and
wherein the non-insulated tip has a shape and height configured to penetrate the patient's skin to bypass one or more of or sweat gland of the patient's skin;
at least one return electrode; and
a controller comprising:
a non-transitory memory storing instructions; and
a processor configured to access the non-transitory memory and to execute the instructions to at least:
deliver an electrical waveform with a set of stimulation parameters to one or more independently addressable electrodes in the array of electrodes; and
deliver another electrical waveform with another set of stimulation parameters to one or more other independently addressable electrodes in the array of electrodes,
wherein the stimulator is configured to emit a shaped and focused electrical field for stimulation of a target tissue based on the electrical waveform and the other electrical waveform.

15. A system comprising:
a stimulator comprising an array of independently addressable electrodes configured to be positioned on a patient's skin, each electrode of the array of electrodes is configured for transcutaneous stimulation;
at least one return electrode;
one or more digital-to-analog converters (DACs);
an output stage comprising one or more transistors;
one or more programmable gain amplifiers (PGAs) coupled to the one or more DACs;
a high pass filter coupled to the output stage; and
a controller comprising:
a non-transitory memory storing instructions; and
a processor configured to access the non-transitory memory and to execute the instructions to at least:
deliver an electrical waveform with a set of stimulation parameters to one or more independently addressable electrodes in the array of electrodes; and
deliver another electrical waveform with another set of stimulation parameters to one or more other independently addressable electrodes in the array of electrodes,
wherein the stimulator is configured to emit a shaped and focused electrical field for stimulation of a target tissue based on the electrical waveform and the other electrical waveform,
wherein the electrical waveform and the other electrical waveform are directly configured as a function of base/gate voltage of the one or more transistors, and
wherein a current or voltage output is delivered between the one or more DACs and the one or more PGAs to drive the one or more transistors of the output stage through the high pass filter.

16. The system of claim 15, further comprising:
a discharge switch coupled to an output of the stimulator and the return electrode,
wherein the discharge switch is shorted to the return electrode at an end of each delivery of the electrical waveform and/or the other electrical waveform to remove any residual charge when necessary.

17. The system of claim 15, further comprising:
an impedance measurement circuit coupled to an output of the stimulator;
wherein the processor is further configured to execute the instructions to:
measure an electrode-tissue impedance; and
adaptively adjust a compliance voltage of the stimulator as a function of a known stimulation intensity and the measured electrode-tissue impedance.

18. The system of claim 17, wherein the processor is further configured to execute the instructions to measure conductivity between any two electrodes of the array of electrodes to determine if a short circuit has formed.

19. The system of claim 17, wherein the processor is further configured to execute the instructions to monitor a respiration rate of the patient from the measured electrode-tissue impedance.

20. The system of claim 15, wherein the instruction to measure an electrode-tissue impedance comprises injecting a sinusoidal or square current into the target tissue and measuring an evoked electrode bio-potential.

* * * * *